United States Patent
Fan et al.

(10) Patent No.: US 10,591,422 B2
(45) Date of Patent: Mar. 17, 2020

(54) APPARATUS AND METHOD FOR INCREASING DYNAMIC RANGE OF A PARTICLE SENSOR

(71) Applicant: Honeywell International Inc., Morris Plains, NJ (US)

(72) Inventors: Xiao Zhu Fan, Plymouth, MN (US); Matthew Wiebold, Northfield, MN (US); Jason Garde, Anthem, AZ (US); Lee R Wienkes, Morris Plains, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 100 days.

(21) Appl. No.: 15/725,687

(22) Filed: Oct. 5, 2017

(65) Prior Publication Data

US 2019/0107496 A1    Apr. 11, 2019

(51) Int. Cl.
| | |
|---|---|
| *G01N 21/94* | (2006.01) |
| *G01N 21/47* | (2006.01) |
| *G01J 1/04* | (2006.01) |
| *G01N 15/02* | (2006.01) |
| *G01N 15/06* | (2006.01) |

(Continued)

(52) U.S. Cl.
CPC ............ *G01N 21/94* (2013.01); *G01J 1/0462* (2013.01); *G01N 15/0205* (2013.01); *G01N 15/0211* (2013.01); *G01N 15/06* (2013.01); *G01N 15/1456* (2013.01); *G01N 21/47* (2013.01); *G01N 15/1434* (2013.01); *G01N 2015/0046* (2013.01); *G01N 2015/0294* (2013.01); *G01N 2015/0693* (2013.01); *G01N 2015/1447* (2013.01); *G01N 2021/945* (2013.01); *H04B 10/11* (2013.01)

(58) Field of Classification Search
CPC ..................................................... G01N 21/94
USPC ............................................................ 356/338
See application file for complete search history.

(56) References Cited

U.S. PATENT DOCUMENTS

| | | | | |
|---|---|---|---|---|
| 4,934,811 A | * | 6/1990 | Watts | G01N 21/8507 250/227.11 |
| 4,953,978 A | * | 9/1990 | Bott | G01N 15/0211 356/336 |

(Continued)

FOREIGN PATENT DOCUMENTS

| | | |
|---|---|---|
| WO | 2007046875 A2 | 4/2007 |
| WO | 2009149498 A1 | 12/2009 |

(Continued)

OTHER PUBLICATIONS

Li et al., "Dynamic Light Scattering", "http://cnx.org/content/m50236/1.2/", May 8, 2014, pp. 1-13, Publisher: OpenStax-CNX module: m50236.

(Continued)

*Primary Examiner* — Tarifur R Chowdhury
*Assistant Examiner* — Omar H Nixon
(74) *Attorney, Agent, or Firm* — Fogg & Powers LLC

(57) ABSTRACT

A particle detection system is provided. The particle detection system comprises at least one transmitter; at least one receiver; a first interrogation volume formed by a first intersection of a first pair of a transmitter beam of a transmitter and a receiver field of view of a receiver; and a second interrogation volume formed by a second intersection of a second pair of a transmitter beam of a transmitter and a receiver field of view of a receiver.

20 Claims, 11 Drawing Sheets

(51) Int. Cl.
*G01N 15/14* (2006.01)
*H04B 10/11* (2013.01)
*G01N 15/00* (2006.01)

(56) References Cited

U.S. PATENT DOCUMENTS

| | | | |
|---|---|---|---|
| 5,110,204 A * | 5/1992 | Miles | G01P 5/20 356/28 |
| 5,502,561 A | 3/1996 | Hutchins et al. | |
| 5,528,045 A * | 6/1996 | Hoffman | G01N 15/14 250/458.1 |
| 5,835,211 A * | 11/1998 | Wells | G01N 15/0205 356/336 |
| 6,831,279 B2 * | 12/2004 | Ho | G01N 21/6486 250/458.1 |
| 8,047,055 B2 | 11/2011 | Wang et al. | |
| 8,358,411 B2 | 1/2013 | Babico et al. | |
| 8,634,072 B2 | 1/2014 | Trainer | |
| 2002/0159060 A1 | 10/2002 | Roques et al. | |
| 2003/0142311 A1 | 7/2003 | Molter et al. | |
| 2004/0144935 A1 * | 7/2004 | Xu | G01N 15/0211 250/573 |
| 2005/0243307 A1 * | 11/2005 | Silcott | G01N 15/1459 356/73 |
| 2006/0061753 A1 * | 3/2006 | Harris | G01S 7/4811 356/4.05 |
| 2006/0078998 A1 * | 4/2006 | Puskas | G01N 21/6428 436/64 |
| 2007/0242269 A1 | 10/2007 | Trainer | |
| 2008/0013076 A1 | 1/2008 | Matsui | |
| 2008/0021674 A1 * | 1/2008 | Puskas | G01N 15/1429 702/179 |
| 2008/0158543 A1 | 7/2008 | Puskas et al. | |
| 2008/0231854 A1 | 9/2008 | Seifert et al. | |
| 2009/0039249 A1 * | 2/2009 | Wang | G01N 15/0205 250/287 |
| 2009/0088982 A1 * | 4/2009 | Fukushima | C12Q 1/6825 702/23 |
| 2010/0038534 A1 * | 2/2010 | Hendrich | H01J 37/20 250/307 |
| 2010/0051804 A1 * | 3/2010 | Adamec | H01J 37/244 250/307 |
| 2010/0288921 A1 * | 11/2010 | Wang | G01N 15/0205 250/287 |
| 2012/0008143 A1 * | 1/2012 | Ihlefeld | G01N 15/0205 356/335 |
| 2012/0244532 A1 * | 9/2012 | Craighead | B01L 3/502761 435/6.11 |
| 2012/0245047 A1 * | 9/2012 | Craighead | B01L 3/502761 506/9 |
| 2013/0342684 A1 | 12/2013 | Keranen et al. | |
| 2014/0330459 A1 | 11/2014 | Baumgardner et al. | |
| 2017/0315045 A1 * | 11/2017 | Silcott | G01N 15/1434 |
| 2018/0073974 A1 * | 3/2018 | Diebold | G01N 15/1434 |

FOREIGN PATENT DOCUMENTS

| | | |
|---|---|---|
| WO | 2016058699 A1 | 4/2016 |
| WO | 2017060105 A1 | 4/2017 |

OTHER PUBLICATIONS

European Patent Office, "Partial European Search Report for EP Application No. 18198519.3" dated Mar. 28, 2019, Foreign Counterpart to U.S. Appl. No. 15/725,687, pp. 1-17, Published EP.

* cited by examiner

APPARATUS AND METHOD FOR INCREASING DYNAMIC RANGE OF A PARTICLE SENSOR

BACKGROUND

Particles such as volcanic ash and supercooled water droplets can detrimentally affect aircraft performance. These particles typically have mean volumetric diameters (MVDs) of about fifty microns.

The supercooled water droplets form ice when contacting, e.g. an airfoil, of an aircraft. Icing of airfoils has caused aircraft catastrophes. Many modern aircraft are designed to include ice protected surfaces and fly in conditions of icing arising from supercooled water droplets of fifty microns or less.

There exist supercooled large water droplets having MVDs up to five thousand microns. Aircraft are not typically designed to fly in conditions of icing arising from supercooled large water droplets because such larger droplets (a) adhere to more of the aircraft surface than smaller droplets and (b) are more likely to move behind ice protected surfaces.

Because aircraft are not protected from supercooled large water droplets, it is important for an aircraft to detect their presence so that the aircraft and/or its pilot can take action to avoid resulting icing. Modern particle sensors using optical transceiver systems are not typically designed to detect the presence of particles having MVDs with a dynamic range of one thousand while maintaining adequate detection sensitivity over the particle size range. Typical high dynamic range particle detection systems unsatisfactorily sacrifice detection sensitivity, e.g. for relatively small sized particles, to increase particle size detection dynamic range. For example, this can result in an undesirable tradeoff—facilitating detection of large particles while diminishing the detection accuracy of small particles, such as volcanic ash—which could lead to aircraft engine damage or even failure. Therefore, there is a need for a particle detector that has both high dynamic range of particle detection size, while maintaining adequate detection sensitivity over the particle size range.

SUMMARY

In one embodiment, a particle detection system is provided. The particle detection system comprises at least one transmitter; at least one receiver; a first interrogation volume formed by a first intersection of a first pair of a transmitter beam of a transmitter and a receiver field of view of a receiver; and a second interrogation volume formed by a second intersection of a second pair of a transmitter beam of a transmitter and a receiver field of view of a receiver.

In another embodiment, another particle detection system is provided. The other particle detection system comprises a transmitter; a receiver; an interrogation volume formed by an intersection of a transmitter beam of the transmitter and the receiver field of view of the receiver; and at least one amplifier system, coupled to the receiver, configured to output at least two signals each of which has been amplified by different gain levels.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments. Reference characters denote like elements throughout figures and text.

DETAILED DESCRIPTION

Figure 1:
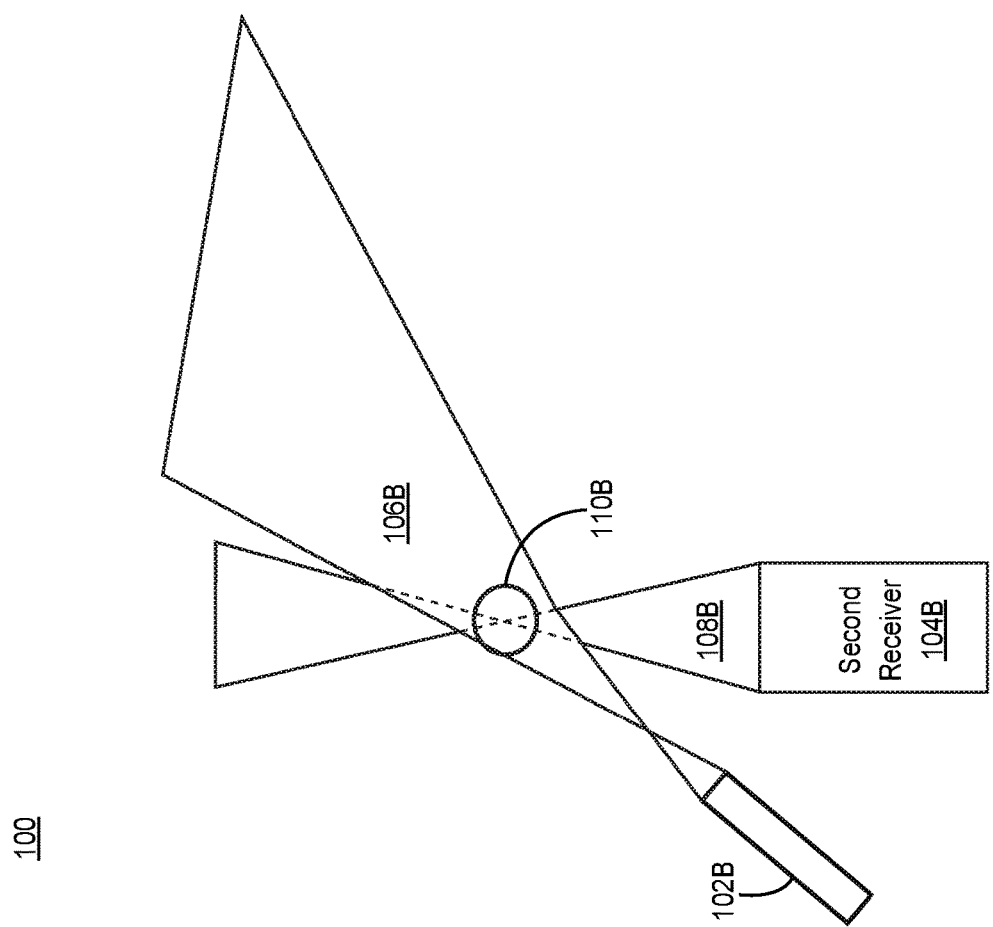
FIG. 1 illustrates a block diagram of one embodiment of a system comprising two pairs of transmitters and receivers.
Figure 1:
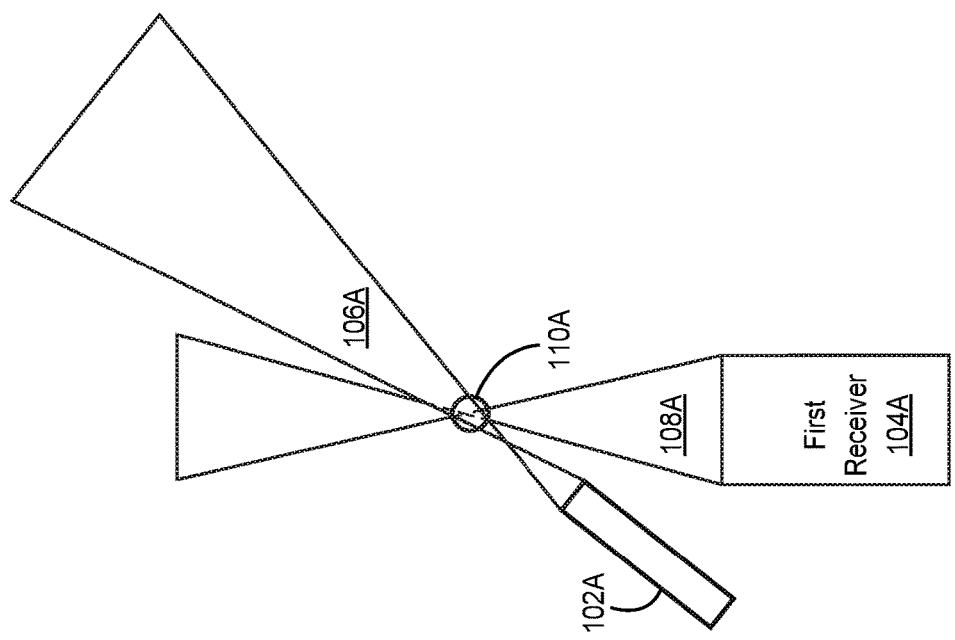

In the following detailed description, reference is made to the accompanying drawings that form a part hereof, and in which is shown by way of illustration specific illustrative embodiments. However, it is to be understood that other embodiments may be utilized and that structural, mechanical, and electrical changes may be made. Furthermore, the method presented in the drawing figures and the specification is not to be construed as limiting the order in which the individual steps may be performed. The following detailed description is, therefore, not to be taken in a limiting sense.

The illustrated embodiments may be used in vehicles for particle detection. For some vehicles, such as aircraft, the volume may be located in undisturbed space, e.g. undisturbed from the fluid flow (such as airflow) around the vehicle. Alternatively, the illustrated embodiments can be used for other applications such as monitoring particulates in exhaust of smoke stacks, and in catalytic reactors.

In one embodiment, the invention uses two or more interrogation volumes to increase dynamic range and maintain a broad range of sensitivity. An interrogation volume is a volume in which particles are characterized. In another embodiment, two detector dynamic ranges can be used. Both embodiments will be subsequently described.

For pedagogical reasons, for the embodiment with at least two interrogation volumes, two interrogation volumes will be subsequently described. One interrogation volume is relatively small, and in which particles having a relatively small mean volumetric diameter (MVD) (or a smaller MVD) are characterized. The other interrogation volume is relatively large, and in which particles having a relatively large MVD (or a larger MVD) are characterized.

However, more than two interrogation volumes can be used. If more than two interrogation volumes are used, then then the volume of each additional region is, e.g., correspondingly scaled between the size of the interrogation volumes used to characterize immediately smaller and immediately large particles.

Smaller interrogation volumes are used to characterized smaller particles because the intensity of optical energy radiated from an optical source, e.g. a LASER, can be higher in the smaller volume, particularly for example if the electromagnetic energy is focused. More light energy is scattered by the smaller particles and received by an optical receiver, and thus sensitivity is maintained across the detection spectrum of small to large particles. The optical energy received by a receiver can be used to characterize the particles, e.g. size and shape. Larger volumes are necessary to accurately perform such characterizations of larger particles. The foregoing systems can be used to characterize particles having MVDs ranging from three to one thousand microns, one to five thousand microns, or even broader ranges.

Different techniques for characterizing particles in two or more interrogation volumes will now be described. FIG. 1 illustrates a block diagram of one embodiment of a system comprising two pairs of transmitters and receivers (first system) 100. For pedagogical reasons, the transmitters described herein are optical transmitters such as LASERs, and the receivers described herein are optical receivers. In another embodiment, the optical transmitters and receivers operate at single frequencies or over a narrow bandwidth, e.g., to improve receiver signal to noise ratio.

For pedagogical reasons, the subsequently illustrated transmitters are exemplified having focused optical beams, and the subsequently illustrated receivers are exemplified has having fields of view with focal points. Alternatively, the transmitters can have divergent or collimated optical beams; receivers can have fields of view that are divergent or collimated. In another embodiment, the transmitter beam and the receiver field of view occur in free space.

The first system 100 comprises a first transmitter 102A, a second transmitter 102B, a first receiver 104A, and a second receiver 104B. The first transmitter 102A has a first transmitter beam 106A which is focused. The second transmitter 102B has a second transmitter beam 106B which is focused. The first receiver 104A has a first receiver field of view 108A which is focused. The second receiver 104B has a second receiver field of view 108B which is focused. As exemplified for all illustrated systems, the focal length of each beam is adjusted to create interrogation volumes of different sizes.

The first transmitter beam 106A and the first receiver field of view 108A overlap, or intersect, creating a first interrogation volume 110A. The second transmitter beam 106B and the second receiver field of view 108B overlap, or intersect, creating a second interrogation volume 110B. The volume of the second interrogation volume 110B is greater than the volume of the first interrogation volume 110A; alternatively, as will be subsequently be illustrated the volumes of the first interrogation volume 110A and the second interrogation volume 110B can be designed so that the former is larger than the latter. In one embodiment, the first interrogation volume 110A and the second interrogation volume 110B are proximate to one another so that the characterization of small and large particles is made in about the same region.

Light is scattered by particles having relatively small MVDs in the first interrogation volume 110A back along the first receiver field of view 108A to the first receiver 104A.

Light is scattered by particles having relatively large MVDs in the second interrogation volume 110B back along the second receiver field of view 108B to the second receiver 104B.

For the systems illustrated herein, parameters of transmitter and receiver components such as lens parameters, slit parameters, and detectors (e.g. amplifier gain) may vary depending upon corresponding volume of an interrogation volume and a size of particles being detected in such interrogation volume. An exemplary receiver will now be described.

Figure 2:
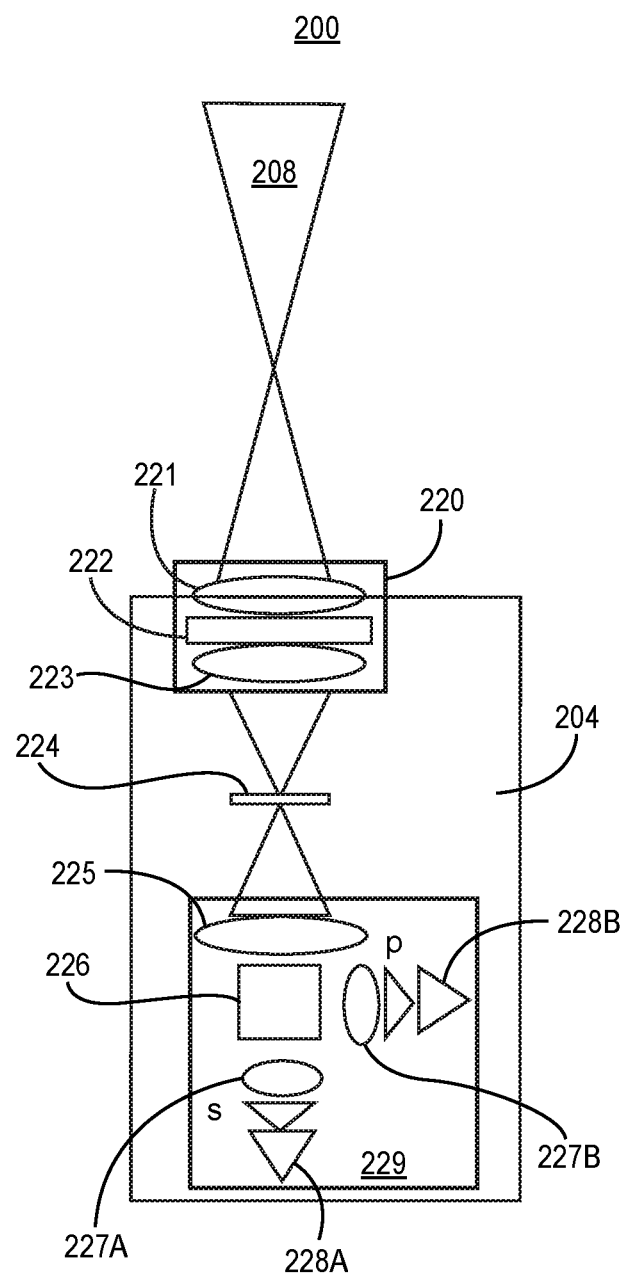
FIG. 2 illustrates a block diagram of one embodiment of a receiver.

FIG. 2 illustrates a block diagram of one embodiment of a receiver (first receiver) 200. The receiver field of view 208, an optical beam, of the first receiver 200 is also illustrated; the receiver field of view 208 corresponds to light scattered by particles in an interrogation volume formed, in part, by the receiver field of view 208. The illustrated optical receiver includes collection optics 220, a first slit 224, and a first optical detection system 229.

The collection optics 220 defines and collects light through the receiver field of view 208 for processing by the rest of the first receiver 200. In one embodiment, the collection optics 220 includes a collection lens 221, a solar filter 222, and/or a first focusing lens 223. In another embodiment, the collection optics 220 includes one or more mirrors that direct the optical beam 208 so that the optical receiver 208 need not be in line with the optical beam 208. For purposes of clarity, the collection optics 220 can include one or more of the aforementioned components, and/or other components.

The operation of one embodiment of collection optics 220, including a collection lens 221, a solar filter 222, and a first focusing lens 223, will now be described. The collection lens 221 collimates received light from the optical beam 208; the collimated light propagates to the solar filter 222.

The solar filter 222 filters out all light except for the optical wavelengths emitted by transmitter(s), e.g. of the systems described herein; the solar filter 222 improves the signal to noise ratio of the receiver. The first focusing lens focuses the collimated, filtered light (propagated through the solar filter 222) on to the first slit 224. The first slit 224 is designed to remove a portion of scattered light from the edge of the optical beam 208 so that scattered light from the most uniform part of the optical beam 208 is detected; this enhances measurement accuracy. The slit 224 may also be used to define the length and height of a corresponding interrogation volume.

The filtered light, after passing through the first slit 224, impinges the first optical detection system 229. In one embodiment, the first receiver 200 detects the presence of particles of a particular MVD, or range of MVDs, in a corresponding interrogation volume when the first optical detection system 229 detects the presence of light. In another embodiment, the first optical detection system 229 determines the intensity and/or polarization of such light. The intensity and/or polarization respectively correspond to, and can be subsequently processed to determine, the number of such particles, and the shape of such particles.

In one embodiment, the first optical detection system 229 comprises a collimating lens 225, a polarizing beam splitter 226, a second focusing lens 227A, a first optical, or S, detector 228A, a third focusing lens 227B, and a second optical, or P, detector 228B. The collimating lens 225 collimates the light that passes through the first slit 224 and impinges upon the collimating lens 225.

The polarizing beam splitter 226 separates linear polarized light so that light which is substantially parallel with the light emitted by the transmitter(s) (p polarization) is directed along path p, and light which is substantially perpendicular with the light emitted by the transmitter(s) (s polarization) is directed along path s. If the detected light scattered by particles substantially has p polarization then the particles are substantially spherical in shape. The intensity of light scattered with s polarization (relative to the intensity of light scattered with p polarization) indicates the degree to which the particles (which scatters the light) are aspherical.

The second focusing lens 227A focuses collimated light of a first (s) polarization in the s path onto the S detector 228A. The third focusing lens 227B focuses collimated light of a second (p) polarization in the p path onto the P detector 228B. Each of the S detector 228A and the P detector 228B comprise a photodetector and signal processing electronics (such as filters, amplifiers, and/or analog to digital converters). The photodetectors may be any type of photodetectors, including photoelectric or photovoltaic detectors. One example of a photoelectric detector that may be used is an avalanche photodiode. In one embodiment, detector(s), e.g. the S detector 228A and the P detector 228B, used to detect smaller particles have greater sensitivities then the corresponding detectors used to detect larger particles.

The first optical detection system 229 can be implemented differently. In an alternative embodiment, the first optical detection system 229 can be implemented using the components illustrated in FIG. 2, but excluding the polarizing beam splitter 226, the second focusing lens 227B, and the P detector 228B. As a result, the S detector 228A will detect scattered light of all polarizations, including S and P polarizations. This embodiment can be used to determine the amount, but not the shape, of particles in a corresponding interrogation volume.

Figure 3:
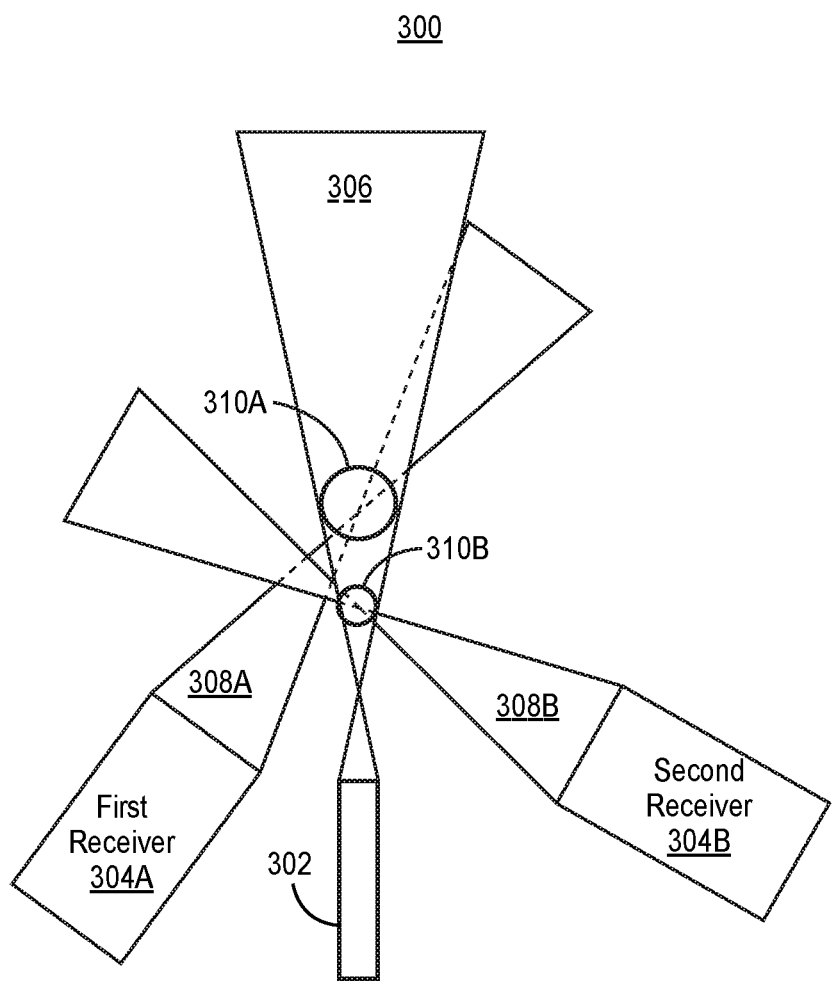
FIG. 3 illustrates a block diagram of one embodiment of a system comprising one transmitter and two receivers.

FIG. 3 illustrates a block diagram of one embodiment of a system comprising one transmitter and two receivers (second system) 300. The second system 300 includes a transmitter 302, a first receiver 304A, and a second receiver 304B. The transmitter 302 has a transmitter beam 306 which is focused. The first receiver 304A has a first receiver field of view 308A which is focused. The second receiver 304B has a second receiver field of view 308B which is focused.

The transmitter beam 306 and the first receiver field of view 108A overlap, or intersect, creating a first interrogation volume 310A. The transmitter beam 306 and the second receiver field of view 308B overlap, or intersect, creating a second interrogation volume 310B. The volume of the second interrogation volume 310B is smaller than the volume of the first interrogation volume 310A. In one embodiment, the first interrogation volume 310A and the second interrogation volume 310B are proximate to one another so that the characterization of large and small particles is made in about the same region.

Light is scattered by particles having relatively large MVDs in the first interrogation volume 310A back along the first receiver field of view 308A to the first receiver 304A. Light is scattered by particles having relatively small MVDs in the second interrogation volume 310B back along the second receiver field of view 308B to the second receiver 304B.

Figure 4:
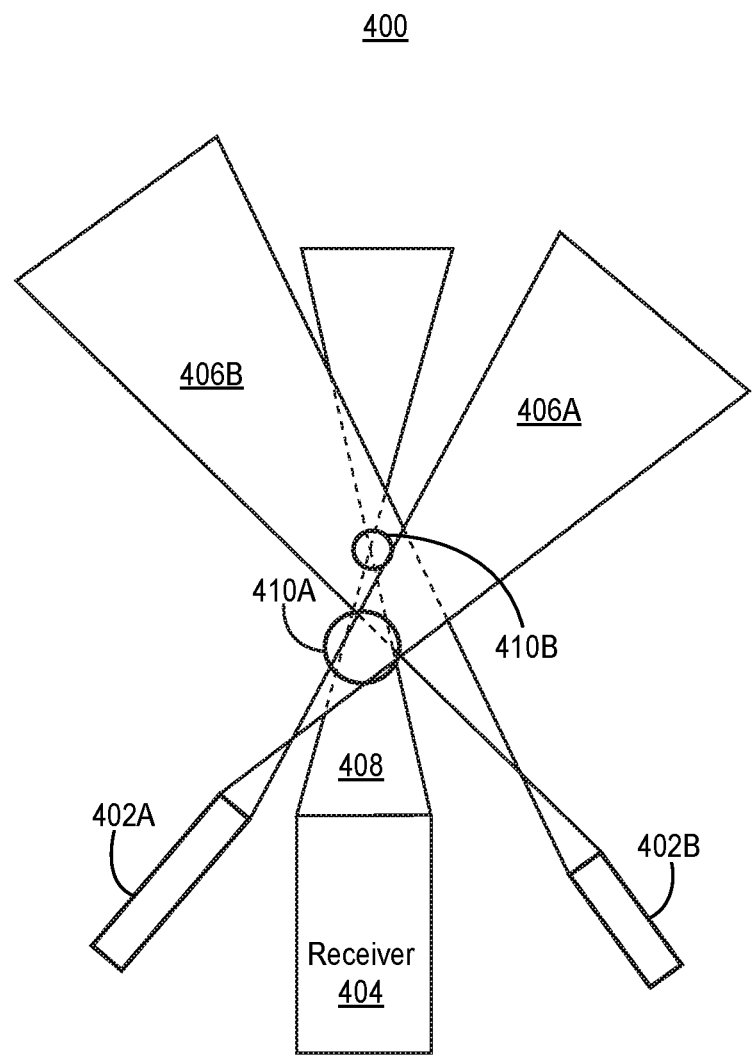
FIG. 4 illustrates a block diagram of one embodiment of a system comprising two transmitters and one receiver.

FIG. 4 illustrates a block diagram of one embodiment of a system comprising two transmitters and one receiver (third system) 400. The third system 400 includes a first transmitter 402A, a second transmitter 402B, and a receiver 404. The first transmitter 402A has a first transmitter beam 406A which is focused. The second transmitter 402B has a second transmitter beam 406B which is focused. The receiver 404 has a receiver field of view 408 which is focused.

The first transmitter beam 406A and the receiver field of view 408 overlap, or intersect, creating a first interrogation volume 410A. The second transmitter beam 406B and the receiver field of view 408 overlap, or intersect, creating a second interrogation volume 410B. The volume of the second interrogation volume 410B is smaller than the volume of the first interrogation volume 410A. In one embodiment, the first interrogation volume 410A and the second interrogation volume 410B are proximate to one another so that the characterization of large particles and small particles is made in about the same region.

Light is scattered by particles having relatively large MVDs in the first interrogation volume 410A back along the receiver field of view 408 to the receiver 404. Light is scattered by particles having relatively small MVDs in the second interrogation volume 410B back along the receiver field of view 408 to the receiver 404.

Figure 5:
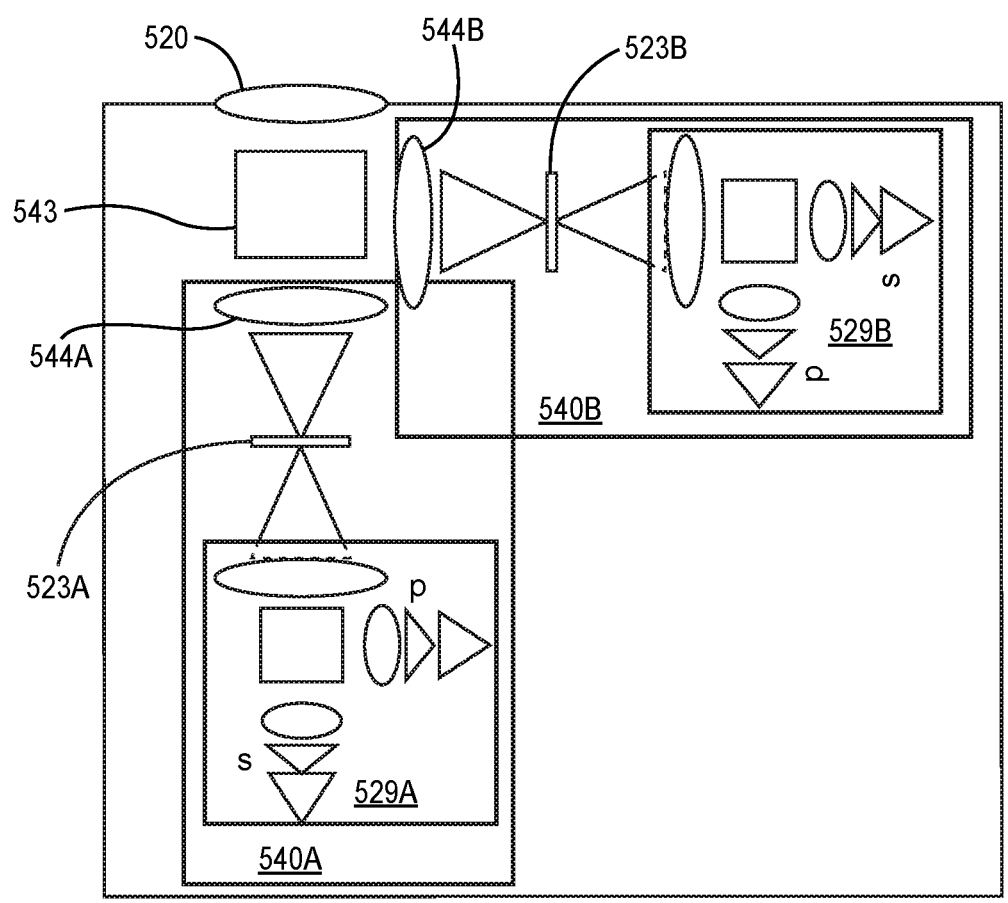
FIG. 5 illustrates one embodiment of a receiver configured to receive optical signals of two different wavelengths.

In one embodiment, the receiver 404 discriminates between scattering from the first interrogation volume 410A and the second interrogation volume 410B because the first transmitter 402A and the second transmitter 402B transmit light of different wavelengths. FIG. 5 illustrates one embodiment of a receiver configured to receive optical signals of two different wavelengths, e.g. 905 nm and 1550, (dichromatic receiver or second receiver) 500.

The illustrated dichromatic receiver 500 comprises collection optics 520, a dichromatic beam splitter 543, a first receiver system 540A, and a second receiver system 540B. The receiver field of view 408 impinges the collection optics 520. In one embodiment, the collection optics 520 includes a lens and a solar filter, and projects collimated light upon a dichromatic beam splitter 543. The lens facilitates the receiver field of view 408 to be focused. In another embodiment, the collection optics 520 includes one or more mirrors that direct the receiver field of view 408 so that the receiver 408 need not be in line with the receiver field of view 408.

The dichromatic beam splitter 543, e.g. a dichromatic prism, directs light of different wavelengths in different directions, for example to the first receiver system 540A and the second receiver system 540B. The first receiver system 540A processes and detects light of a first wavelength (or a first narrow band of wavelengths). The first receiver system 540A comprises a fourth focusing lens 544A, a second slit 523A, and a second optical detection system 529A. The fourth focusing lens 544A, the second slit 523A, and the first optical detection system 529A function in an analogous manner as described above for the first focusing lens 223, the first slit 224, and the first optical detection system 229.

The second receiver system 540B processes and detects light of a second wavelength (or a second narrow band of wavelengths). The second receiver system 540B comprises a fifth focusing lens 544B, a third slit 523B, and a third optical detection system 529B. The fifth focusing lens 544B, the third slit 523B, and the second optical detection system 529B function in an analogous manner as described above for the first focusing lens 223, the first slit 224, and the first optical detection system 229.

Figure 6:
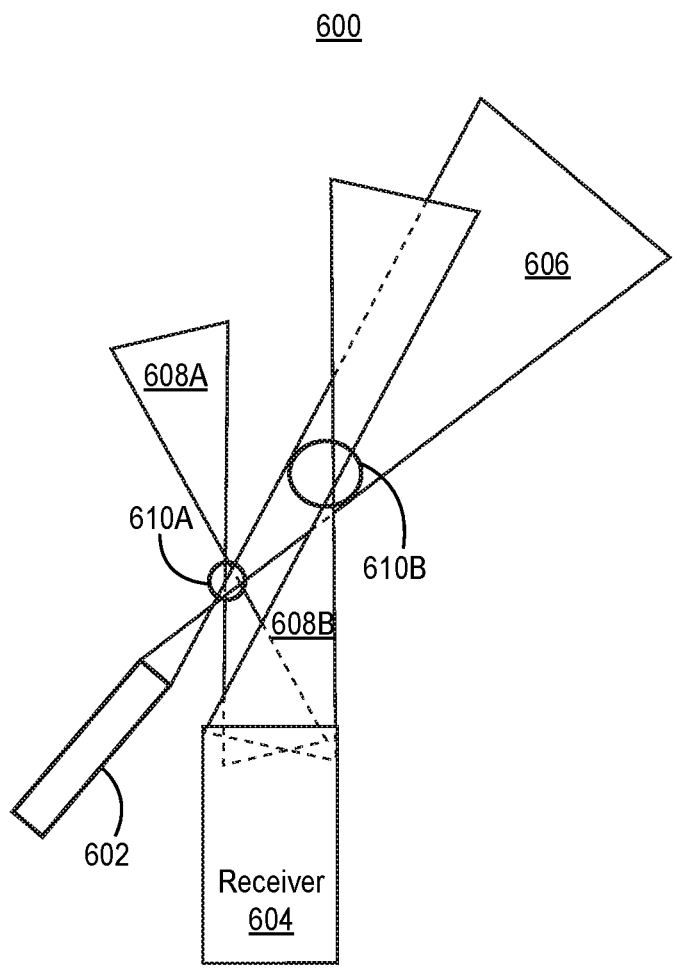
FIG. 6 illustrates a block diagram of one embodiment of a system comprising one transmitter and one receiver.

FIG. 6 illustrates a block diagram of one embodiment of a system comprising one transmitter and one receiver (fourth system) 600. The fourth system 600 includes a transmitter 602 and a receiver 604. The transmitter 602 has a first transmitter beam 606 which is focused. The receiver 604 has a first receiver field of view 608A and a second receiver field of view 608B both of which are focused. The first receiver field of view 608A and the second receiver field of view 608B may occur simultaneously or sequentially as will be further described below.

The transmitter beam 606 and the first receiver field of view 608A overlap, or intersect, creating a first interrogation volume 610A. The transmitter beam 606 and the second receiver field of view 608B overlap, or intersect, creating a second interrogation volume 610B. The volume of the first interrogation volume 610A is smaller than the volume of the second interrogation volume 610B. In one embodiment, the first interrogation volume 610A and the second interrogation volume 610B are proximate to one another so that the characterization of small and large particles is made in about the same region.

Light is scattered by particles having relatively small MVDs in the first interrogation volume 610A back along the first receiver field of view 608A to the receiver 604. Light is scattered by particles having relatively large MVDs in the second interrogation volume 610B back along the second receiver field of view 608B to the receiver 604.

In one embodiment, the first receiver field of view 608A and the second receiver field of view 608B occur sequentially at different times. In another embodiment, the more than two receiver field of views may occur, e.g. in a specific order, at different times.

The sequencing of the receiver field of views may be accomplished by moving the receiver 604 or component(s) of the receiver 604 with an electric motor and/or a piezoelectric motor. For example, the whole collection lens 221 or just mirrors (described above) in the collection lens 221 may be periodically moved. In one embodiment, the receiver 604 can be moved between more than two positions to create more than more than two receiver field of views, and thus, interrogation volumes. Alternatively, electro-optical devices, such as an electro-optical modulator, can be used to sequence the receiver field of views using electrical control, e.g. voltage, signals.

The time that a receiver field of view occurs varies based upon environment. In upper atmospheric conditions where fewer large particles exist, the second receiver field of view 608B will occur for a significantly longer time, e.g. ninety percent of a time period, whereas the first receiver field of view 608A would occur for a shorter time, e.g. ten percent of the time period. In environments where there is an equal distribution of large and small particles, then the duty cycle (corresponding to time of occurrence for the first receiver field of view 608B and the second receiver field of view 608B) may be fifty percent.

Figure 7:
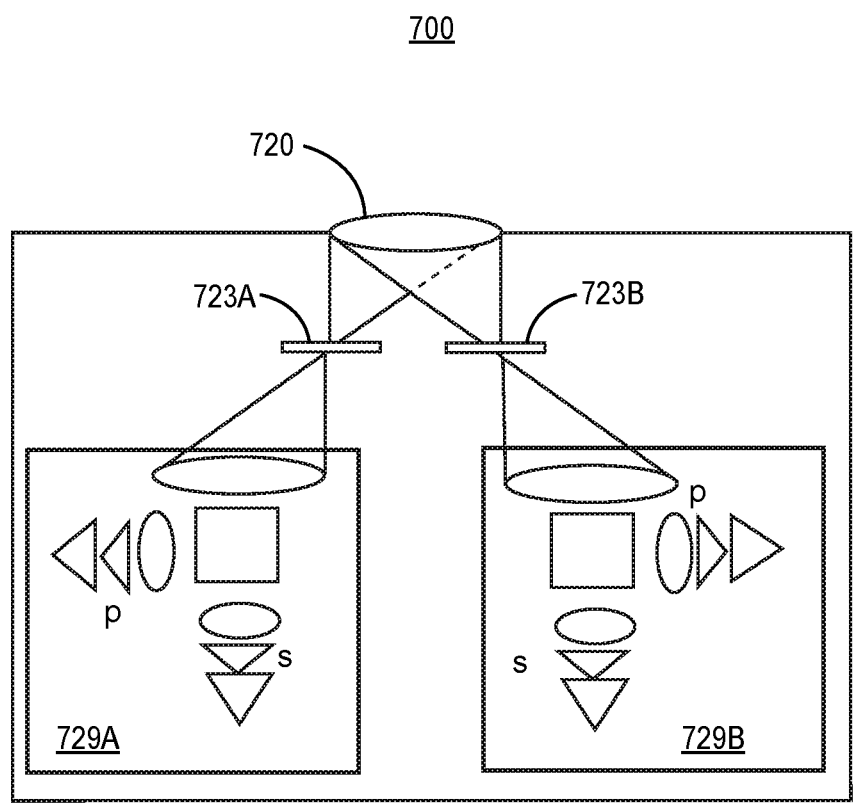
FIG. 7 illustrates a block diagram of one embodiment of a receiver having two simultaneous receiver field of views.

Alternatively, in another embodiment, the receiver 604 has a first receiver field of view 608A and a second receiver field of view 608B which occur simultaneously. This can be implemented by another type of receiver design. FIG. 7 illustrates a block diagram of one embodiment of a receiver having two simultaneous receiver field of views (third receiver) 700. The illustrated third receiver 700 comprises collection optics 720, a fourth slit 723A, a fifth slit 723B, a first receiver system 729A, and a second receiver system 729B. The fourth slit 723A and the fifth slit 723B are offset from the centerline of the collection optics 720. As a result, the second receiver field of view 608B and the first receiver field of view 608A are also correspondingly projected at such angles from the centerline. Thus, the second receiver field of view 608B impinges upon the collection optics 720, and is focused upon the fourth slit 723A. In one embodiment, the collection optics 720 includes the same components which are described as being included in the collection optics 220 of FIG. 2.

The fourth slit 723A, which performs the same function as described above for the first slit 223A, projects—at the same angle as the second receiver field of view 608B is projected through the collection optics 720—the second receiver field of view 608B onto a fourth optical detection system 729A. The fourth optical detection system 729A processes the second receiver field of view 608B in a manner similar as described above for the first optical detection system 229 of FIG. 2.

Further, the first receiver field of view 608A impinges upon the collection optics 720, and is focused upon the fifth slit 723B. The fifth slit 723B, which performs the same function as described above for the first slit 223A, projects—at the same angle as the first receiver field of view 608A is projected through the collection optics 720—the first receiver field of view 608A onto a fifth optical detection system 729B. The fifth optical detection system 729B processes the first receiver field of view 608A in a manner similar as described above for the first optical detection system 229 of FIG. 2.

Figure 8:
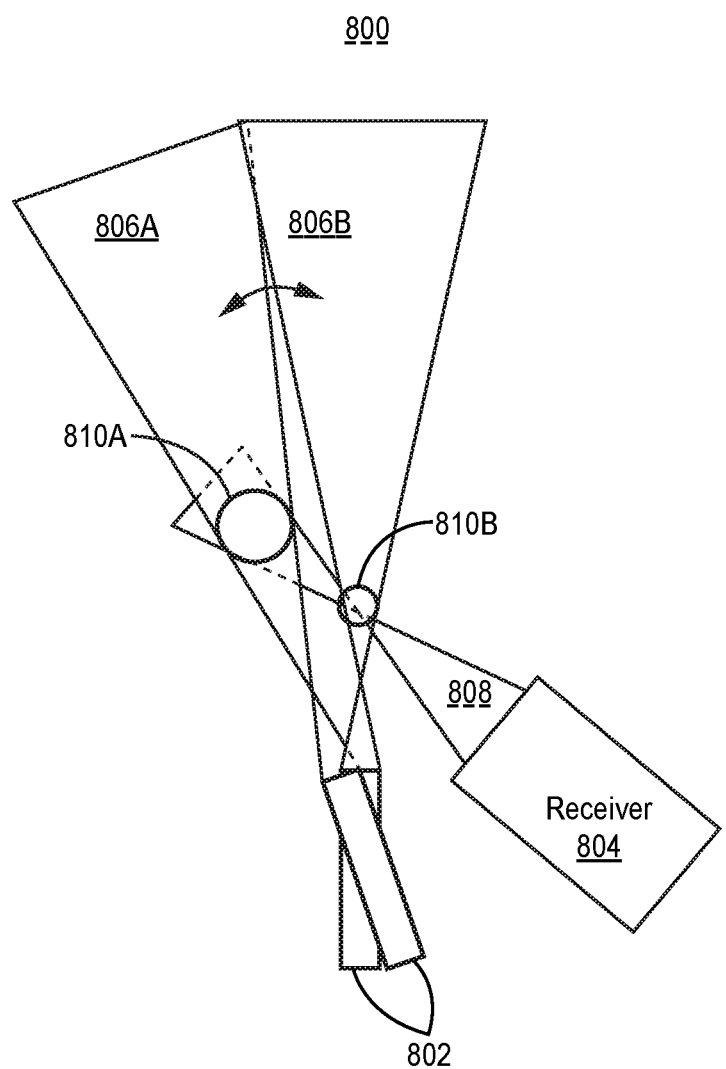
FIG. 8 illustrates a block diagram of another embodiment of a system comprising one transmitter and one receiver.

Alternatively, when a single transmitter and a single receiver are used, two or more transmitter beams can occur at different times, e.g. by moving the transmitter or component(s) thereof. FIG. 8 illustrates a block diagram of another embodiment of a system comprising one transmitter and one receiver (fifth system) 800. The fifth system 800 comprises a transmitter 802 and a receiver 804. The transmitter 802, or component(s) thereof, are moved between at least two positions so that at least a first transmitter beam 806A and a second transmitter beam 806B occur and are sequenced. The receiver 804 has a receiver field of view 808. In another embodiment, the transmitter 802, or component(s) thereof are moved by periodically moving the transmitter 802 or component(s) of the transmitter 802 with an electric motor and/or a piezoelectric motor. For example, lens(es) and/or mirror(s) in the transmitter 802 may be periodically moved. Alternatively, electro-optical devices such as an electro-optical modulator, can be used to sequence the transmitter beams using electrical control, e.g. voltage, signals.

The first transmitter beam 806A and the receiver field of view 808A overlap, or intersect, creating a first interrogation volume 810A. The second transmitter beam 806A and the receiver field of view 808 overlap, or intersect, creating a second interrogation volume 810B. The volume of the first interrogation volume 810A is larger than the volume of the second interrogation volume 810B. In one embodiment, the first interrogation volume 810A and the second interrogation volume 810B are proximate to one another so that the characterization of small and large particles is made in about the same region.

Light is scattered by particles having relatively large MVDs in the first interrogation volume 810A back along the receiver field of view 808 to the receiver 804. Light is scattered by particles having relatively small MVDs in the second interrogation volume 810B back along the receiver field of view 808 to the receiver 804.

The time that a transmitter beam occurs varies based upon environment. In upper atmospheric conditions where fewer large particles exist, the first transmitter beam 806A will be used for a significantly longer period, e.g. consuming ninety percent of a time period, than the second transmitter beam 806B, e.g. consuming ten percent of the time period. In environments where there is an equal distribution of large and small particles, then the duty cycle would be, e.g., fifty percent. In one embodiment, the transmitter beam can be moved between more than two positions to create more than more than two interrogation volumes.

Figure 9:
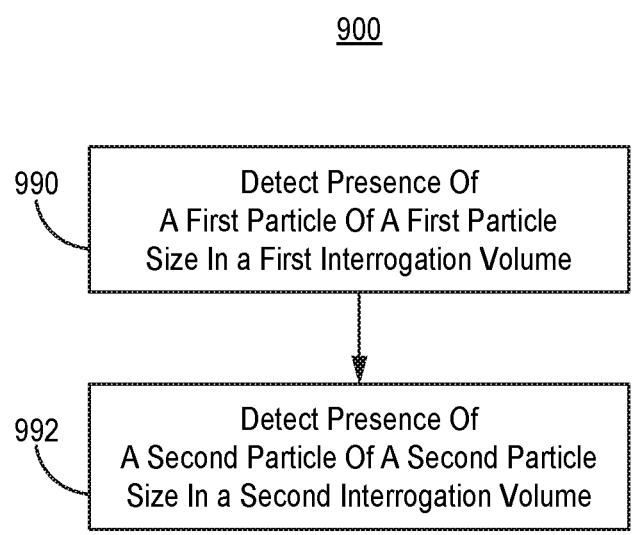
FIG. 9 illustrates one embodiment for increasing dynamic range of a particle sensor while maintaining broad range of sensitivity.

FIG. 9 illustrates one embodiment for increasing dynamic range of a particle sensor while maintaining broad range of sensitivity 900. To the extent that the embodiment of method 900 shown in FIG. 9 is described herein as being implemented in the systems shown in FIGS. 1 through 8, and 10, it is to be understood that other embodiments can be implemented in other ways. The blocks of the flow diagrams have been arranged in a generally sequential manner for ease of explanation; however, it is to be understood that this arrangement is merely exemplary, and it should be recognized that the processing associated with the methods (and the blocks shown in the Figure) can occur in a different order (for example, where at least some of the processing associated with the blocks is performed in parallel and/or in an event-driven manner).

In block 990, detect a presence of a first particle of a first particle size in a first interrogation volume. In one embodiment, detecting the presence of the first particle of the first particle size in the first interrogation volume comprises detecting during a first time period. In another embodiment, detecting the presence of the first particle of the first particle size in the first interrogation volume comprises detecting at least one of (a) intensity of the scattered light and (b) relative polarization of the scattered light.

In block 992, detect a presence of a second particle of a second particle size in a second interrogation volume. In one embodiment, detecting the presence of the second particle of the second particle size in the second interrogation volume comprises detecting during a second time period subsequent to the first time period. In another embodiment, the first time period and the second time period sequentially repeat. In a further embodiment, the duty cycle is smaller for the time period corresponding to an interrogation volume used to detect larger particles. In yet another embodiment, detecting the presence of the second particle of the second particle size in the second interrogation volume comprises detecting at least one of (a) intensity of scattered light and (b) relative polarization of the scattered light. In yet a further embodiment, blocks 990 and 992 are performed by at least one transmitter, e.g. a LASER, and at least one receiver, e.g. an optical receiver.

Figure 10:
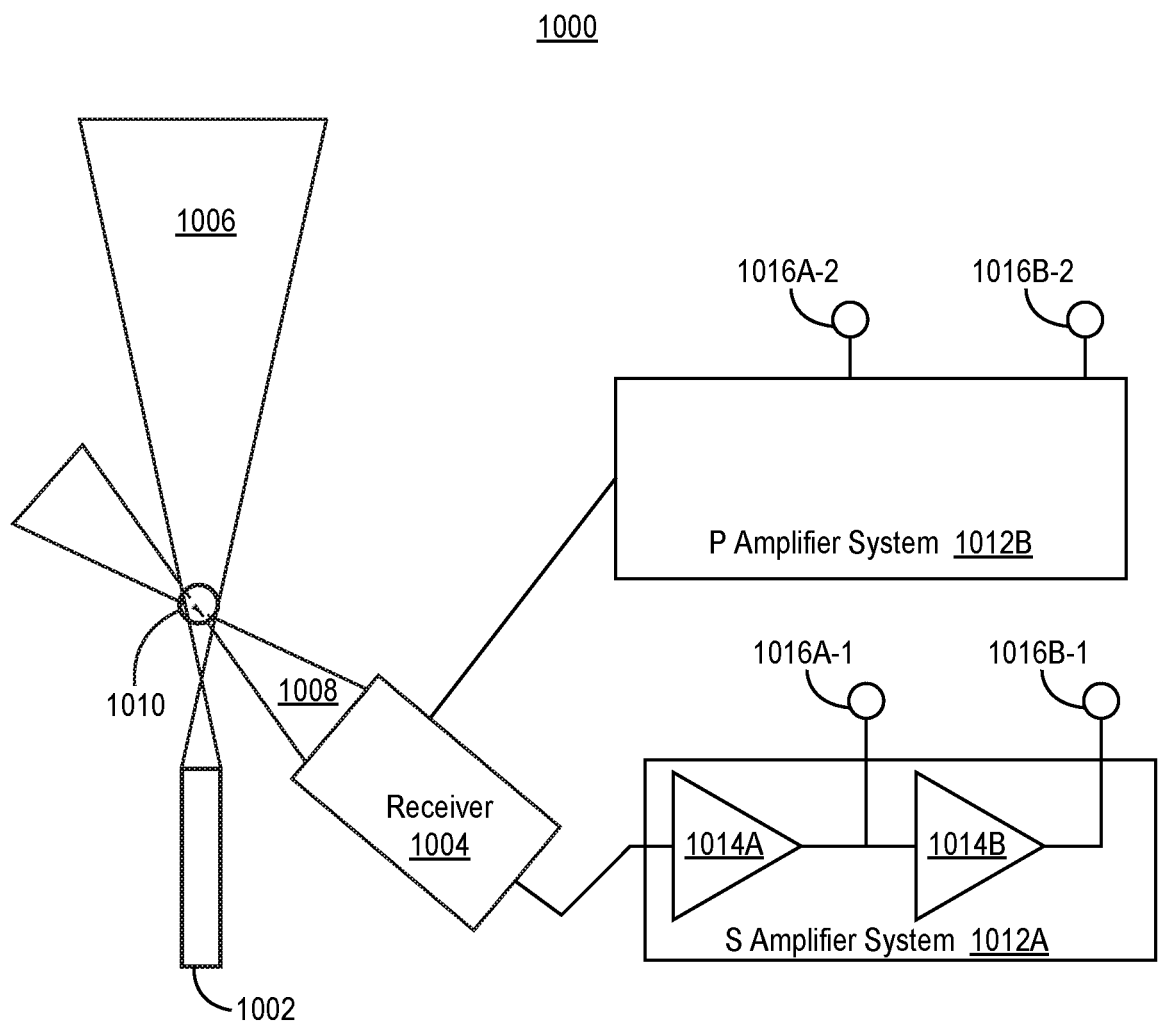
FIG. 10 illustrates a block diagram of another embodiment of a system comprising one transmitter and one receiver.

FIG. 10 illustrates a block diagram of another embodiment of a system comprising one transmitter and one receiver (sixth system) 1000. The sixth system 1000 comprises a transmitter 1002 and a receiver 1004 respectively having a transmitter beam 1006 and a receiver field of view 1008.

In one embodiment, the transmitter 1002 is implemented as described above, and has a fixed position. In another embodiment, the receiver 1004 is implemented as described above with respect to FIG. 2.

The transmitter beam 1006 and the receiver field of view 1008 overlap, or intersect, creating an interrogation volume 1010. The interrogation volume 1010 is used to characterize both small and large particles, and is sized accordingly.

Light is scattered by particles having relatively large MVDs in the interrogation volume 1010 back along the receiver field of view 1008 to the receiver 1004. Light is also scattered by particles having relatively small MVDs in the interrogation volume 1010 back along the receiver field of view 1008 to the receiver 1004.

The output of the receiver 1004, e.g. an output of an optical detection system, is coupled to one or more amplifier systems. As illustrated in FIG. 10, an S amplifier system 1012A and a P amplifier system 1012B are coupled to the output of the receiver 1004, e.g. respectively to the outputs of an S detector 228A and a P detector 228B. The S amplifier system 1012A has at least one output, e.g. a first output 1016A-1 and a second output 1016A-2. The P amplifier system 1012B has at least one output, e.g. a first output 1016BA-1 and a second output 1016B-2. As is illustrated below, each amplifier system may only have a single output. Further, if only a single detector is used, as described above, then only one amplifier system is coupled to the output of the receiver 1004.

The implementation and operation of an exemplary amplifier system, the first amplifier system 1012A, will now be described. The first amplifier system 1012A has a first output 1016A-1 and a second output 1016B-1. The second output 1016B-1 has a higher dynamic range than the first output 1016A-1. The difference in dynamic range occurs because the signals at the first output 1016A-1 and the second output 1016B-1 are substantially identical versions of a signal from the output of the receiver 1004 except that the signal at the first output 1016A-1 has been amplified less than the signal at the second output 1016B-1. In one embodiment, the amplifier system 1012A comprises at least two series coupled amplifiers, e.g. a first amplifier 1014A and a second amplifier 1014B. The first output 1016A-1 is coupled to the output of an amplifier, e.g. the first amplifier 1014A, preceding one or more other amplifiers in the amplifier system 1012A. The second output 1016B-1 is coupled to the output of an amplifier, e.g. the second amplifier 1014B, succeeding one or more other amplifiers in the amplifier system 1012A. The gain associated with the preceding amplifiers is lower than the gain associated with the succeeding amplifiers. Outputs having relatively lower gains, e.g. the first output 1016A-1, are used to amplify signals corresponding to relatively larger particles. Outputs have relatively higher gains, e.g. the second output 1016B-1, are used to amplify signals corresponding to relatively smaller particles. Each of the amplifier systems 1012A, 1012B illustrated in FIG. 10 may alternatively be implemented by at least one variable gain amplifier (VGA) whose gain may be varied over time. As a result, an amplifier system 1012A with a variable gain amplifier can have a single output that generates signals amplified by two or more gain levels and which correspond to different particle sizes as described above. The duty cycle of such gains may be as described above with respect to FIG. 3.

Figure 11:
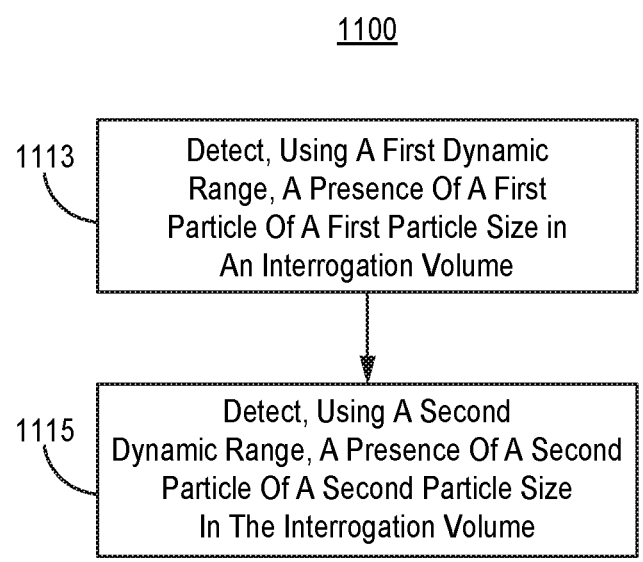
FIG. 11 illustrates another embodiment for increasing dynamic range of a particle sensor while maintaining broad range of sensitivity.

FIG. 11 illustrates another embodiment for increasing dynamic range of a particle sensor while maintaining broad range of sensitivity 1100. To the extent that the embodiment of method 1100 shown in FIG. 1 is described herein as being implemented in the systems shown in FIGS. 1 through 8, and 10, it is to be understood that other embodiments can be implemented in other ways. The blocks of the flow diagrams have been arranged in a generally sequential manner for ease of explanation; however, it is to be understood that this arrangement is merely exemplary, and it should be recognized that the processing associated with the methods (and the blocks shown in the Figure) can occur in a different order (for example, where at least some of the processing associated with the blocks is performed in parallel and/or in an event-driven manner).

In block 1113, detect a presence of a first particle of a first particle size in a first interrogation volume. In one embodiment, detecting the presence of the first particle of the first particle size in the first interrogation volume comprises detecting during a first time period. In another embodiment, detecting the presence of the first particle of the first particle size in the first interrogation volume comprises detecting at least one of (a) intensity of scattered light and (b) relative polarization of scattered light.

In block 1115, detect a presence of a second particle of a second particle size in the first interrogation volume. In one embodiment, detecting the presence of the second particle of the second particle size in the first interrogation volume comprises detecting during a second time period subsequent to the first time period. In another embodiment, the first time period and the second time period sequentially repeat. In a further embodiment, the duty cycle is smaller for the for the time period corresponding to an interrogation volume used to detect larger particles. In yet another embodiment, detecting the presence of the second particle of the second particle size in the first interrogation volume comprises detecting at least one of (a) intensity of scattered light and (b) relative polarization of the scattered light. In yet a further embodiment, blocks 990 and 992 are performed by at least one transmitter, e.g. a LASER, and at least one receiver, e.g. an optical receiver.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

EXAMPLE EMBODIMENTS

Example 1 includes a particle detection system, comprising: at least one transmitter; at least one receiver; a first interrogation volume formed by a first intersection of a first pair of a transmitter beam of a transmitter and a receiver field of view of a receiver; and a second interrogation volume formed by a second intersection of a second pair of a transmitter beam of a transmitter and a receiver field of view of a receiver.

Example 2 includes the particle detection system of Example 1, wherein the at least one receiver is configured to: detect a presence of a first particle of a first particle size in the first interrogation volume; and detect presence of a second particle of a second particle size in the second interrogation volume.

Example 3 includes the particle detection system of Examples 1-2, wherein detect the presence of the first particle comprises detect at least one of (a) an intensity of scattered light and (b) a relative polarization of the scattered light; and where detect the presence of the second particle comprises detect at least one of (a) an intensity of scattered light and (b) a relative polarization of the scattered light.

Example 4 includes the particle detection system of Example 1, wherein the at least one receiver comprises an optical receiver comprising: a slit; collection optics which collects light through the receiver field of view and focuses it upon the slit; and an optical detection system which receives light from the slit.

Example 5 includes the particle detection system of Example 1, wherein the at least one transmitter consists of a transmitter; wherein the transmitter beam of the first pair and the transmitter beam of the second pair are the same transmitter beam; wherein the at least one receiver comprises at least two receivers; and wherein the receiver field of view of the first pair and the receiver field of view of the second pair are different receiver field of views.

Example 6 includes the particle detection system of Example 1, wherein the at least one transmitter comprises at least two transmitters; wherein the transmitter beam of the first pair and the transmitter beam of the second pair are different transmitter beams; wherein the at least one receiver consists of a receiver; and wherein the receiver field of view of the first pair and the receiver field of view of the second pair are the same receiver field of view.

Example 7 includes the particle detection system of Examples 1-6, wherein each of the at least two transmitters generates optical signals having a unique frequency or frequency band; and wherein the one receiver comprises: collection optics which collects light through a receiver field of view and collimates such light; a dichromatic beam splitter configured to direct optical signals of different frequencies or frequency bands in different directions; a first receiver system configured to receive an optical signal of a first frequency or a first frequency band; and a second receiver system configured to receive an optical signal of a second frequency or a second frequency band.

Example 8 includes the particle detection system of Examples 1-7, wherein the first receiver system and the second receiver system each comprise: a slit; a first focusing lens configured to focus collimated light onto the slit; and an optical detection system configured to receive light from the slit.

Example 9 includes the particle detection system of Example 1, wherein the at least one transmitter consists of a transmitter; and wherein the at least one receiver consists of a receiver.

Example 10 includes the particle detection system of Examples 1-9, wherein the receiver comprises: a first slit; a second slit; collection optics which (a) collects light through a first receiver field of view and focuses it upon the first slit, and (b) collects light through a second receiver field of view and focuses it upon the second slit; a first optical detection system which receives light from the first slit; a second optical detection system which receives light from the second slit; wherein the transmitter beam of the first pair and the transmitter beam of the second pair are the same transmitter beam; and wherein the receiver field of view of the first pair is the first receiver field of view and the receiver field of view of the second pair is the second receiver field of view.

Example 11 includes the particle detection system of Examples 1-9, wherein the receiver field of view of the first pair and the receiver field of view of the second pair are sequenced; wherein the transmitter beam of the first pair and the transmitter beam of the second pair are the same transmitter beam; and wherein the receiver field of view of the first pair and the receiver field of view of the second pair are different receiver field of views.

Example 12 includes the particle detection system of Examples 1-9, wherein the transmitter field of view of the first pair and the transmitter field of view of the second pair are sequenced; wherein the receiver field of view of the first pair and the receiver field of view of the second pair are the same receiver field of view; and wherein the transmitter beam of the first pair and the transmitter beam of the second pair are different transmitter beams.

Example 13 includes a method, comprising: detecting presence of a first particle of a first particle size in a first interrogation volume; and detecting presence of a second particle of a second particle size in a second interrogation volume.

Example 14 includes the method of Example 13, further comprising: wherein detecting the presence of the first particle comprises detecting at least one of (a) an intensity of scattered light and (b) a relative polarization of the scattered light; and wherein detecting the presence of the second particle comprises detecting at least one of (a) an intensity of scattered light and (b) a relative polarization of the scattered light.

Example 15 includes the method of Example 13, wherein detecting the presence of the first particle in the first interrogation volume comprises detecting the presence of the first particle sequentially in time with detecting the presence of the second particle.

Example 16 includes a particle detection system, comprising: a transmitter; a receiver; an interrogation volume formed by an intersection of a transmitter beam of the transmitter and the receiver field of view of a receiver; and at least one amplifier system, coupled to the receiver, configured to output at least one signal which has been amplified by different gain levels.

Example 17 includes the particle detection system of Example 16, wherein the at least one amplifier system has at least two outputs.

Example 18 includes a method, comprising: detecting, using a first detection dynamic range, a presence of a first particle of a first particle size in an interrogation volume; and detecting, using a second detection dynamic range, a presence of a second particle of a second particle size in the interrogation volume.

Example 19 includes the method of Example 18, wherein detecting, using the first detection dynamic range, the presence of the first particle comprises detecting at least one of (a) an intensity of scattered light and (b) a relative polarization of the scattered light; and wherein detecting, using the second detection dynamic range, the presence of the second particle comprises detecting at least one of (a) an intensity of scattered light and (b) a relative polarization of the scattered light.

Example 20 includes the method of Examples 18-19, wherein detecting, using the first detection dynamic range, the presence of the first particle in the first interrogation volume comprises detecting the presence of the first particle sequentially in time with detecting, using the second detection dynamic range, the presence of the second particle.

Although specific embodiments have been illustrated and described herein, it will be appreciated by those of ordinary skill in the art that any arrangement, which can achieve the same purpose, may be substituted for the specific embodiments shown. Therefore, it is manifestly intended that this invention be limited only by the claims and the equivalents thereof.

What is claimed is:

1. A particle detection system, comprising:
   at least one transmitter;
   at least one receiver;
   a first interrogation volume formed by a first intersection of a first pair of a transmitter beam of a transmitter and a receiver field of view of a receiver; and
   a second interrogation volume formed by a second intersection of a second pair of a transmitter beam of a transmitter and a receiver field of view of a receiver;
   wherein the first and second interrogation volumes are different from each other either by an intensity of the transmitters or by a sensitivity of the receivers;
   wherein the first and second interrogation volumes are located in the same air stream;
   wherein the at least one receiver is configured to:
      detect a first particle of a first particle size and shape in the first interrogation volume by detecting an intensity of scattered light and a relative polarization of the scattered light; and
      detect a second particle of a second particle size and shape in the second interrogation volume by detecting an intensity of scattered light and a relative polarization of the scattered light.

2. The particle detection system of claim 1, wherein the at least one receiver includes an optical detection system comprising:
   collection optics configured to collect the scattered light through the receiver field of view and collimate the scattered light;
   a polarizing beam splitter configured to receive the collimated light from the collection optics and separate the collimated light into s-polarized light and p-polarized light;
   a first optical detector configured to detect the s-polarized light; and
   a second optical detector configured to detect the p-polarized light.

3. The particle detection system of claim 2, wherein the intensity of scattered light with p-polarization corresponds to particles that are substantially spherical in shape; and
   wherein the intensity of scattered light with s-polarization relative to the intensity of scattered light with p-polarization indicates the degree to which the particles are aspherical.

4. The particle detection system of claim 1, wherein the at least one receiver comprises an optical receiver comprising:
   a slit;
   collection optics which collects light through the receiver field of view and focuses it upon the slit; and
   an optical detection system which receives light from the slit.

5. The particle detection system of claim 1, wherein the at least one transmitter consists of a transmitter;
   wherein the transmitter beam of the first pair and the transmitter beam of the second pair are the same transmitter beam;
   wherein the at least one receiver comprises at least two receivers; and
   wherein the receiver field of view of the first pair and the receiver field of view of the second pair are different receiver field of views.

6. The particle detection system of claim 1, wherein the at least one transmitter comprises at least two transmitters;
   wherein the transmitter beam of the first pair and the transmitter beam of the second pair are different transmitter beams;
   wherein the at least one receiver consists of a receiver; and
   wherein the receiver field of view of the first pair and the receiver field of view of the second pair are the same receiver field of view.

7. The particle detection system of claim 6, wherein each of the at least two transmitters generates optical signals having a unique frequency or frequency band; and
   wherein the receiver comprises:
      collection optics which collects light through a receiver field of view and collimates such light;
      a dichromatic beam splitter configured to direct optical signals of different frequencies or frequency bands in different directions;
      a first receiver system configured to receive an optical signal of a first frequency or a first frequency band; and
      a second receiver system configured to receive an optical signal of a second frequency or a second frequency band.

8. The particle detection system of claim 7, wherein the first receiver system and the second receiver system each comprise:
a slit;
a first focusing lens configured to focus collimated light onto the slit; and
an optical detection system configured to receive light from the slit.

9. The particle detection system of claim 1, wherein the at least one transmitter consists of a transmitter; and
wherein the at least one receiver consists of a receiver.

10. The particle detection system of claim 9, wherein the receiver comprises:
a first slit;
a second slit;
collection optics which (a) collects light through a first receiver field of view and focuses it upon the first slit, and (b) collects light through a second receiver field of view and focuses it upon the second slit;
a first optical detection system which receives light from the first slit;
a second optical detection system which receives light from the second slit;
wherein the transmitter beam of the first pair and the transmitter beam of the second pair are the same transmitter beam; and
wherein the receiver field of view of the first pair is the first receiver field of view and the receiver field of view of the second pair is the second receiver field of view.

11. The particle detection system of claim 9, wherein the receiver field of view of the first pair and the receiver field of view of the second pair are sequenced;
wherein the transmitter beam of the first pair and the transmitter beam of the second pair are the same transmitter beam; and
wherein the receiver field of view of the first pair and the receiver field of view of the second pair are different receiver field of views.

12. The particle detection system of claim 9, wherein a transmitter field of view of the first pair and a transmitter field of view of the second pair are sequenced;
wherein the receiver field of view of the first pair and the receiver field of view of the second pair are the same receiver field of view; and
wherein the transmitter beam of the first pair and the transmitter beam of the second pair are different transmitter beams.

13. A method, comprising:
forming a first interrogation volume by a first intersection of a first pair of a transmitter beam of a transmitter and a receiver field of view of a receiver;
forming a second interrogation volume by a second intersection of a second pair of a transmitter beam from a transmitter and a receiver field of view of a receiver;
detecting a presence of a first particle of a first particle size and shape in the first interrogation volume by detecting an intensity of scattered light and a relative polarization of the scattered light; and
detecting a presence of a second particle of a second particle size and shape in the second interrogation volume by detecting an intensity of scattered light and a relative polarization of the scattered light;
wherein the first and second interrogation volumes are different from each other either by an intensity of the transmitters or by a sensitivity of the receivers;
wherein the first and second interrogation volumes are located in the same air stream.

14. The method of claim 13, further comprising:
wherein the intensity of scattered light with p-polarization corresponds to particles that are substantially spherical in shape; and
wherein the intensity of scattered light with s-polarization relative to the intensity of scattered light with p-polarization indicates the degree to which the particles are aspherical.

15. The method of claim 13, wherein detecting the presence of the first particle in the first interrogation volume comprises detecting the presence of the first particle sequentially in time with detecting the presence of the second particle.

16. A particle detection system, comprising:
a transmitter;
a receiver;
an interrogation volume formed by an intersection of a transmitter beam of the transmitter and a receiver field of view of the receiver; and
at least one amplifier system, coupled to the receiver, configured to output at least one signal which has been amplified by different gain levels;
wherein the at least one amplifier system is configured to:
detect, using a first detection dynamic range of a first gain stage, a presence of a first particle of a first particle size and shape in the interrogation volume by detecting an intensity of scattered light and a relative polarization of the scattered light; and
detect, using a second detection dynamic range of a second gain stage, a presence of a second particle of a second particle size and shape in the interrogation volume by detecting an intensity of scattered light and a relative polarization of the scattered light;
wherein data collection related to the first and second particles occurs simultaneously in the receiver.

17. The particle detection system of claim 16, wherein the at least one amplifier system has at least two outputs.

18. A method, comprising:
detecting, using a first detection dynamic range of a first gain stage, a presence of a first particle of a first particle size and shape in an interrogation volume by detecting an intensity of scattered light and a relative polarization of the scattered light; and
detecting, using a second detection dynamic range of a second gain stage, a presence of a second particle of a second particle size and shape in the interrogation volume by detecting an intensity of scattered light and a relative polarization of the scattered light.

19. The method of claim 18, wherein the intensity of scattered light with p-polarization corresponds to particles that are substantially spherical in shape; and
wherein the intensity of scattered light with s-polarization relative to the intensity of scattered light with p-polarization indicates the degree to which the particles are aspherical.

20. The method of claim 19, wherein detecting, using the first detection dynamic range of the first gain stage, the presence of the first particle comprises detecting the presence of the first particle sequentially in time with detecting, using the second detection dynamic range of the second gain stage, the presence of the second particle.

* * * * *